United States Patent [19]

Tolkoff et al.

[11] Patent Number: 5,607,407
[45] Date of Patent: Mar. 4, 1997

[54] CATHETER ASSEMBLY

[76] Inventors: Marc J. Tolkoff, 39 Jordan Rd., Brookline, Mass. 02146; Fernando A. de Toledo, 229 Fairhaven Hill, Concord, Mass. 01742

[21] Appl. No.: 514,945

[22] Filed: Aug. 14, 1995

Related U.S. Application Data

[63] Continuation-in-part of Ser. No. 239,713, May 9, 1994, abandoned.

[51] Int. Cl.$^6$ .................................................. A61M 1/00
[52] U.S. Cl. ......................................................... 604/282
[58] Field of Search .......................... 604/264, 280–282, 604/19, 53, 66, 101, 265–270, 273, 274

[56] References Cited

U.S. PATENT DOCUMENTS

| | | | |
|---|---|---|---|
| 3,757,768 | 9/1973 | Kline | 128/2 M |
| 3,841,308 | 10/1974 | Tate | 128/2 M |
| 3,922,378 | 11/1975 | Kline | 427/2 |
| 4,044,765 | 8/1977 | Kline | 128/2 M |
| 4,052,989 | 10/1977 | Kline | 128/349 |
| 4,068,660 | 1/1978 | Beck | 128/214.4 |
| 4,368,730 | 1/1983 | Sharrock | 604/158 |
| 4,540,411 | 9/1985 | Bocicky | 604/169 |
| 4,737,153 | 4/1988 | Shimamura et al. | 604/282 |
| 4,739,768 | 4/1988 | Engelson | 128/658 |
| 4,921,482 | 5/1990 | Hammerslag et al. | 604/95 |
| 4,954,130 | 9/1990 | Edwards | 604/169 |
| 4,998,916 | 3/1991 | Hammerslag et al. | 604/95 |
| 5,037,427 | 8/1991 | Harada et al. | 606/108 |
| 5,108,368 | 4/1992 | Hammerslag et al. | 604/95 |
| 5,135,502 | 8/1992 | Koenig, Jr. et al. | 604/164 |
| 5,176,653 | 1/1993 | Metais | 604/167 |
| 5,180,376 | 1/1993 | Fischell | 604/282 |

OTHER PUBLICATIONS

Fotz, "Evaluation of Implanted Infusion Devices", NITA, vol. 10, pp. 49–51 (Jan./Feb. 1987).

Goodman & Wickham, "Venous Access Devices", Oncology Nursing Forum, vol. 11, No. 5, pp. 16–23 (Sep./Oct. 1984).

May & Davis, "Percutaneous Catheters and Totally Implantable Access Systems", J. of Intravenous Nursing, vol. 11, No. 2, pp. 97–103 (Mar./Apr. 1988).

*Primary Examiner*—Manuel Mendez
*Attorney, Agent, or Firm*—Chester Cekala

[57] ABSTRACT

The present invention relates to catheters for use with subcutaneous access ports for continuous or intermittent infusion therapy. These catheters utilize a pretensioned, helical coil which is incorporated into a flexible cannulated portion. This feature allows the flexible cannula to be bent without kinking under normal use. This flexibility provides a great deal of comfort to the patient. These catheters also incorporate a puncture needle which is positioned axially down the length of the catheter such that the sharp point at the distal end of the needle extends beyond the distal end of the catheter. This combination of a pretensioned, flexible catheter and a puncture needle achieves a stiffness sufficient to penetrate the tough, self-sealing septum used in subcutaneous access ports, yet, once the puncture needle is removed the patient is left with a comfortable alternative to commonly used hypodermic needles. The present invention also relates to improved transcutaneous infusion systems which utilize these catheters.

12 Claims, 7 Drawing Sheets

CATHETER ASSEMBLY

This application is a continuation-in-part of U.S. Ser. No. 08/239,713, filed May 9, 1994, now abandoned.

FIELD OF THE INVENTION

This invention relates to flexible catheters having a rigidifying means. More particularly this invention relates to catheters for use with subcutaneous access ports for continuous or intermittent infusion therapy. The catheters of the present invention achieve penetration of the tough septa used in these subcutaneous access ports, yet become flexible and comfortable to the user when the rigidifying means is disengaged. These subcutaneous ports are most often used in intravenous, intraarterial and intraperitoneal drug delivery. These ports are also used in artificial organs, e.g., a man-made pancreas. This invention also relates to transcutaneous infusion systems and kits utilizing these catheters.

BACKGROUND

Patients who require frequent infusion therapy often opt to have a subcutaneous vascular access port surgically implanted. These ports generally contain a tough, self-sealing septum which is positioned just below the skin. The tough septum is permanently compressed and held in a rigid access port housing which is sutured directly to muscle tissue to prevent movement. The housing confines a sealed reservoir directly beneath the septum. The housing is typically made of titanium, stainless steel, DELRIN® acetal resin, polysulfone or some other biocompatible and drug compatible material. The reservoir communicates with a vein or artery by way of a silicon or polyurethane connector tube. Although most commercial subcutaneous access port systems share these common elements, a variety of different configurations have been proposed. For a further discussion of subcutaneous access port devices see: Foltz, *Evaluation of Implanted Infusion Devices*, NITA, Vol. 10, No. 1, pp. 49–51 (1987); Goodman et al., *Venous Access Devices—An Overview*, Oncol. Nurs. Forum, Vol. 11, No. 5, pp. 16–23 (1984); and, May et al., *Percutaneous Catheters and Totally Implanted Access Systems*, Journal of Intravenous Nursing, Vol. 11, No. 2, pp. 97–103 (1988), incorporated herein by reference.

In practice, a doctor or nurse palpates the skin to find the outer perimeter or rim of the implanted port septum and then inserts a rigid, metal hypodermic needle directly through the skin and through the septum until the bottom of the reservoir is reached. At this point, infusion therapy is initiated. When the needle is removed the septum self-seals.

The self-sealing septa used in these devices are very tough and typically from about 0.200 inches to about 0.500 inches thick. These septa are required to be tough enough to withstand thousands of punctures with a 19, 20, 21 or 22 gauge hypodermic needle and still maintain an effective seal.

Other subcutaneous medical devices utilizing this type of tough, self-sealing septa include hydrocephalus shunts, dialysis grafts and artificial organs; all of which require intermittent introduction and/or removal of fluid material. These septa are typically mounted in a port housing similar to the subcutaneous vascular access port described above.

The use of rigid, stainless steel hypodermic needles in subcutaneous access port applications has several shortcomings. First, hypodermic needles inserted in port septa are very uncomfortable for the patient, particularly for extended infusion regimes. Second, the hypodermic needle tends to rock and move with body motion. This movement can result in the needle dislodging. If the needle partially dislodges, blood or infused liquid is pumped beneath the skin which can cause tissue damage and an increased risk of infection. If the needle totally dislodges, the liquid could contaminate the surrounding area. Furthermore, needle movement can lead to severe septum damage and subsequent leakage. Third, tissue damage can result from the rigid nature of the hypodermic itself.

One attempt to alleviate these problems involves using "L"-shaped, right-angle needles, like the ones found in FIGS. 1 and 2. Unfortunately, the length of the needle arm from the tip to the elbow of the needle must vary from patient to patient.—Obese patients will require deep penetration (FIG. 1), while thinner patients will require shallower penetration (FIG. 2).—Accordingly, healthcare facilities must keep a variety of right-angle needle sizes on hand to accommodate a variety of patient types. Furthermore, the correct right-angle needle size can only be determined by trial and error, often requiring several applications before the healthcare practitioner determines the optimal depth of penetration for a given patient. This practice is still further complicated by the fact that many patients who require infusion therapy often undergo dramatic changes in weight; thus, requiring the healthcare practitioner to reevaluate the correct needle size with every patient visit.

Another shortcoming of rigid needles in general is that they require extensive dressing with gauze and tape or, in the alternative, require a very specialized and expensive infusion set to prevent the dislodging effect described above.

Some have attempted to develop more comfortable, flexible catheters for subcutaneous access ports. One example is Titan Medical's SURECATH™ port access system product which utilizes an elaborate needle inserting device to anchor and insert the flexible tube to the port. This device is described in U.S. Pat. No. 5,135,502 to Koenig, Jr. et al. This device is difficult to use and involves an expensive inserting device.

It is therefore an object of the present invention to provide an improved catheter for subcutaneous access ports which is relatively inexpensive and simple to use, and which overcomes one or more of the above mentioned problems.

Another object is to provide a catheter which incorporates a pretensioned, helical coil in a flexible cannulated portion. This feature allows the flexible tube to be bent without kinking under normal use. The flexible nature of the tube also is significantly more comfortable than conventional rigid catheters. Furthermore, pretensioning the coil helps keep the catheter longitudinally stiff when a puncture needle is positioned axially down the length of its cannula. This stiffness is essential to facilitate needle penetration through the tough, self-sealing septum used in subcutaneous access ports.

These and other objects will be evident to one skilled in the art from the following:

BRIEF SUMMARY OF THE INVENTION

The present invention, in its most rudimentary embodiment, relates to a subcutaneous access port catheter assembly comprising a flexible catheter, said catheter having distal and proximal ends and having an inner wall portion defined by a pretensioned, continuous helical coil and an outer sheathing formed from a tube of smooth, inert flexible plastic material, wherein said sheath is in intimate contact with the outer spiral of said coil; and an elongated puncture needle having a sharp point at the distal end and a knob member at the proximal end, said puncture needle being inserted coaxially down the length of said catheter such that the sharp point at the distal end of the elongated puncture needle extends beyond the distal end of said catheter, wherein the assembly has sufficient rigidity to penetrate the tough septum of a subcutaneous access port and wherein said elongated puncture needle can be removed from said catheter. The needle and coil make a coupled system which is stiffer than either one alone.

A further embodiment of the present invention relates to a transcutaneous infusion system comprising a flexible catheter, said catheter having distal and proximal ends and having an inner wall portion defined by a pretensioned continuous helical coil and an outer sheathing formed from a tube of smooth, inert flexible plastic material, wherein said sheath is in intimate contact with the outer spiral of said coil; and an elongated puncture needle having a sharp point at the distal end and a knob member at the proximal end, said puncture needle being inserted coaxially down the length of said catheter such that the sharp point at the distal end of the elongated puncture needle extends beyond the distal end of said catheter; and a subcutaneous access port comprised of a tough septum sealing one opening of a rigid, hollow housing, said housing further comprising an outlet port, wherein the catheter and needle assembly has sufficient rigidity to penetrate the tough septum of said subcutaneous access port and wherein said elongated puncture needle can be removed from said catheter.

The present invention also relates to a subcutaneous access port catheter assembly comprising a flexible catheter, said catheter having distal and proximal ends and having an inner wall portion defined by a pretensioned, continuous helical coil and an outer sheathing formed from a tube of smooth, inert flexible plastic material, wherein said sheath is in intimate contact with the outer spiral of said coil; a hollow housing member which has a catheter port affixed to the proximal end of said catheter, a septum port and an infused liquid port; membrane seal member which seals the septum port of said housing member; a hub connector; a flexible tube which connects said hub connector to the fluid infusion port of said housing member; and an elongated puncture needle having a sharp point at the distal end and a knob member at the proximal end, said puncture needle being positioned through said membrane seal and coaxially down the length of said catheter such that the sharp point at the distal end of the elongated puncture needle extends beyond the distal end of said catheter.

Finally, the present invention also relates to more complicated transcutaneous infusion systems comprising: a flexible catheter, said catheter having distal and proximal ends and having an inner wall portion defined by a pretensioned, continuous helical coil and an outer sheathing formed from a tube of smooth, inert flexible plastic material, wherein said sheath is in intimate contact with the outer spiral of said coil; a hollow housing member which has a catheter port affixed to the proximal end of said catheter, a septum port and a fluid infusion port; a membrane seal member which seals the septum port of said housing member; a hub connector; a flexible tube which connects said hub connector to the fluid infusion port of said housing member; an elongated puncture needle having a sharp point at the distal end and a knob member at the proximal end, said puncture needle being positioned through said membrane seal and coaxially down the length of said catheter such that the sharp point at the distal end of the elongated puncture needle extends beyond the distal end of said catheter; and a subcutaneous access port comprised of a tough septum sealing one opening of a rigid, hollow housing, said housing further comprising an outlet port to permit fluid from the hollow housing to an artery, vein or other distant body region by way of a surgically implanted flexible tube, wherein the catheter/needle assembly has sufficient rigidity to penetrate the tough septum of said subcutaneous access port and wherein said elongated puncture needle can be removed from said catheter.

BRIEF DESCRIPTION OF THE DRAWINGS

FIG. 4 depicts a conventional (i.e. round wire) coil. FIG. 5 depicts a ribbon-type coil.

DETAILED DESCRIPTION OF THE PREFERRED EMBODIMENTS

As used herein the term "subcutaneous access port" refers to implantable medical devices used for intermittent introduction and/or removal of fluid materials during intravenous, intraarterial, intraepidural and intraperitoneal therapy. Furthermore, the term also refers to access ports integral with implanted artificial organs, implanted pumps or other implanted medical devices, e.g., hydrocephalus shunts and dialysis grafts, which are also used for intermittent introduction and/or removal of fluids.

As used herein the term "transcutaneous infusion system" refers to medical devices comprising subcutaneous access ports in combination with the catheters of the present invention.

Figure 3:
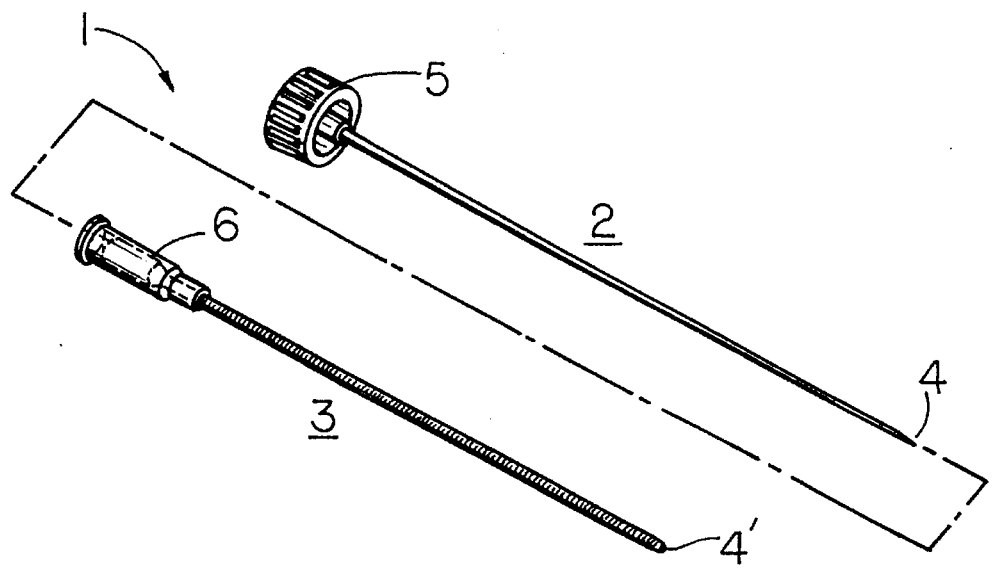
FIG. 3 is an exploded perspective view of a subcutaneous access port catheter assembly in accordance with the present invention.

Referring to FIG. 3, and for illustrative purposes only and not intended to limit the invention and its various applications, a preferred embodiment of the present invention is depicted. FIG. 3 depicts a subcutaneous vascular access port catheter assembly 1 complete with ancillary features for ease of use. The assembly 1 comprises an elongated puncture needle 2 disposed coaxially within a flexible, single-lumen catheter 3 including a pretensioned coil. The length of the catheter 3 is at least slightly shorter than the puncture needle 2. The puncture needle shaft being provided coaxially down the length of the catheter's lumen (as indicated by the broken line) for facilitating the penetration of the distal end of the assembly, 4 and 4', through the skin of the patient and into his/her access port reservoir. The puncture needle 2 is affixed with a sharp point at the distal end 4 and a knob 5 for retracting the needle at its proximal end. The flexible catheter 3 further comprises a hub member 6 at the proximal catheter termination. This hub 6 is for facilitating the connection of the catheter to an external source of intravenous fluid after the puncture needle is removed. The hub 6 can be any suitable connection means, preferably a luer-lock connector. Typically, the hub connector allows for fluid flow from the infusion source to the cannulated cavity.

Figure 4:
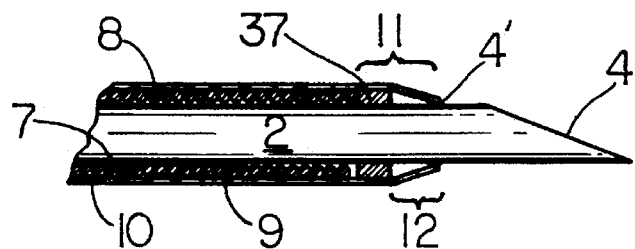
FIGS. 4 and 5 are longitudinal sections of the flexible helical coil catheters constructed in accordance with the principals of the present invention, which further includes an integral penetration needle assembly.
Figure 5:
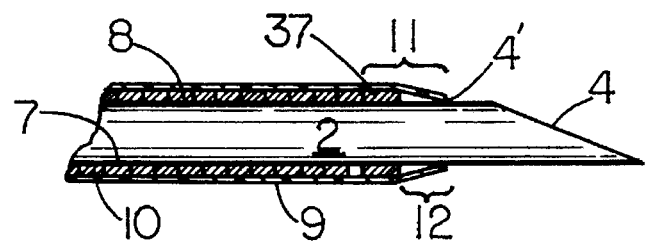

Referring to the diagrams in FIGS. 4 and 5, the distal end of the catheter assembly 1 includes an inner wall portion 7 defined by a continuous helical coil 8 wound with the helices thereof in contact with each other. The coil may be fabricated from wire or filament with a round cross section (See FIGS. 4 and 10), with a flat, ribbon-like cross-section (See FIGS. 5 and 11) or any other geometry which achieves the objects of the present invention.

Figure 1:
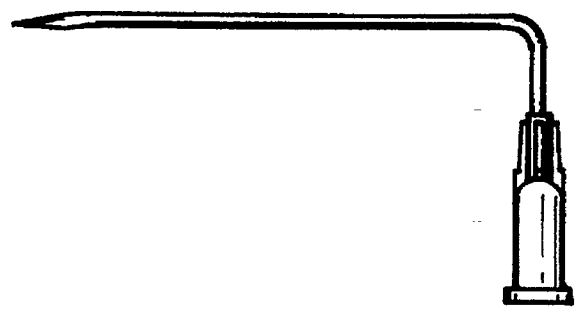
FIG. 1 is a longitudinal cross-sectional view of a conventional "L"-shaped, right-angle needle catheter for use in a subcutaneous access port.
Figure 2:
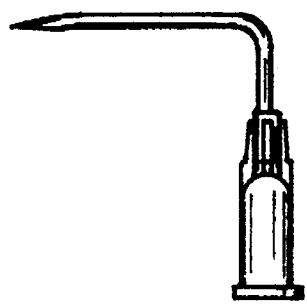
FIG. 2 is a longitudinal cross-sectional view of a another "L"-shaped, right-angle needle catheter. Note the shorter penetration region between the needle tip and the elbow.
Figure 10:
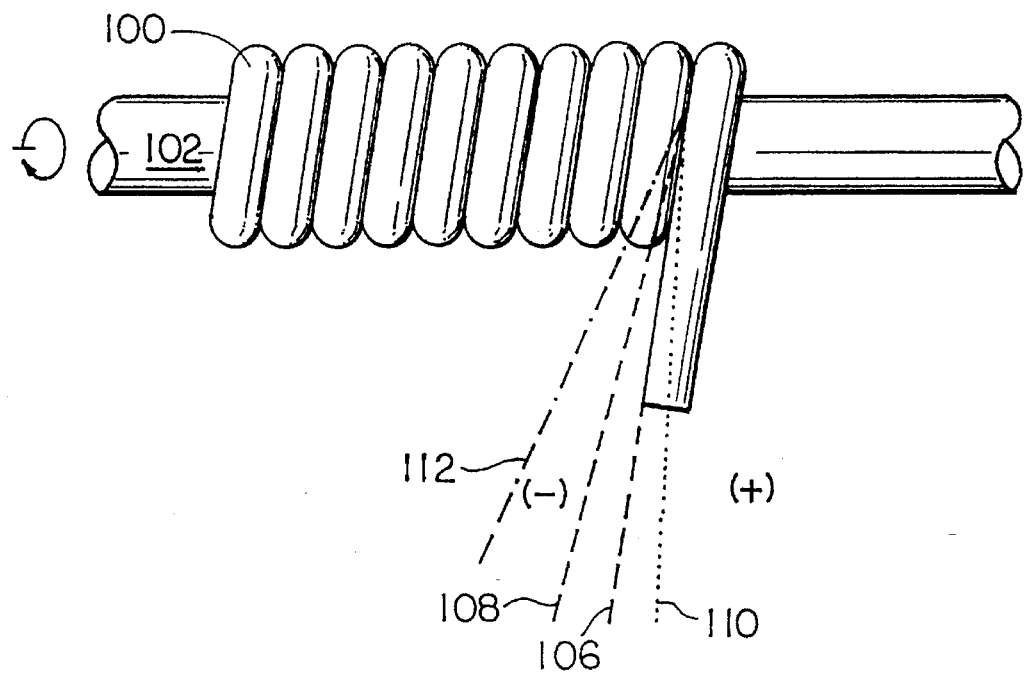
FIGS. 10 and 11 are schematic depictions of the wire-winding technique used to provide the pretensioned coils of the present invention.
Figure 11:
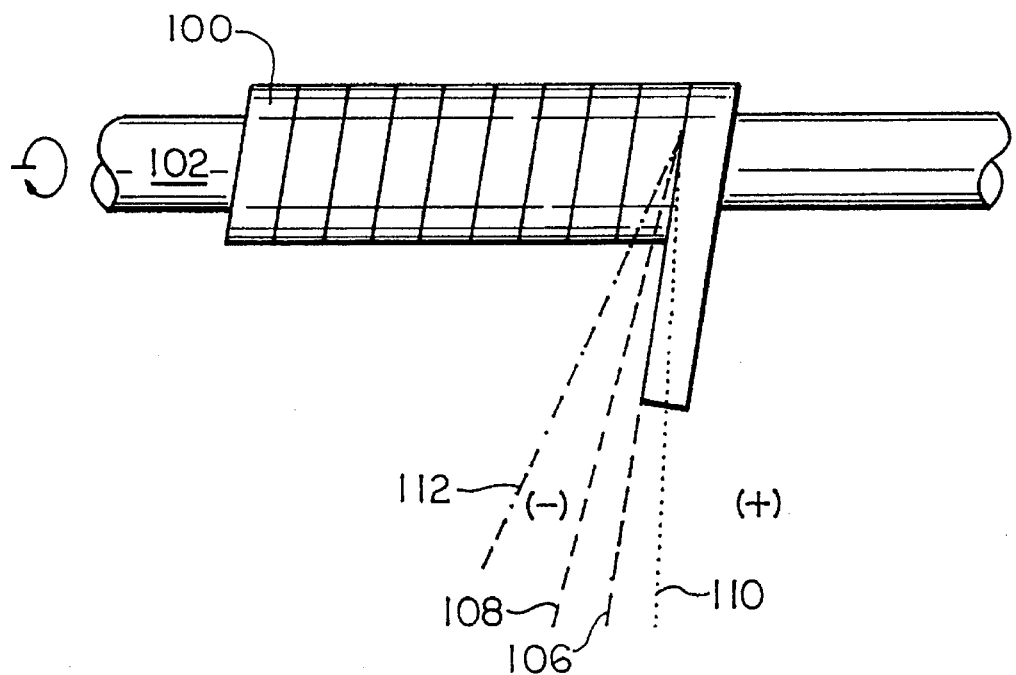

As used herein the term "pretensioned coil" refers to a coil which, when layed out flat on a surface, requires a pulling force to cause separation (i.e. spaces) between individual coil elements. An example of a pretensioned coil is one which is prepared by a mandrel winding technique incorporating a negative lead angle. FIG. 10 depicts a round wire wrap and FIG. 11 depicts a ribbon wire wrap. Referring to FIGS. 10 and 11, a wire 100 is affixed to a rotating mandrel 102. As the helix of the coil develops with each rotation, a coil angle 106 is established transverse to the longitudinal axis of said mandrel. If the wire is advanced at an angle equal to the lead angle, a zero lead angle 108 is produced. If the wire is advanced ahead of the wrapped wire, a positive lead angle 110 is achieved. This results in spaces between the coils as can be seen in FIG. 2 of U.S. Pat. No. 4,044,765 to Kline. These spaces produce a bunching of the tube sheath when compressive forces are applied. Since large compressive forces are necessary to puncture the tough septa of a subcutaneous access port, this type of bunching results in a fatal instability in the catheter which renders it ineffective. If the wire is advanced behind the wrapped wire, a negative lead angle is achieved. Negative lead angle wrapping results in a "pretensioned" coil in accordance with the present invention. Pretensioned coils exhibit greatly improved penetration ability when used in the catheters of the present invention. Preferably the negative lead angle is from 0° to 4°, and most preferably from 2° to 3°. Care must be taken not to use too severe a negative lead angle, as it will result in a doubling over, or overwrapping, of the coil.

A pretensioned coil is required for proper performance of the present catheter. Without it there is no stiffened column effect. Pretensioning of the coil improves the overall stiffness of the catheter assembly under compression. This would be the case when the catheter is being pushed through the tough septum of a vascular access port. This effect can be measured by the following procedure:

1. The catheter is clamped in a pin vise with 1.4 inches exposed.
2. The pin vise is then mounted on the force-arm of an Accu-Force "Cadet" force gauge manufactured by Ametek. The pin vise is oriented such that the catheter tip is perpendicular to the gauge. This enables the user to measure the force necessary to deflect the tip. As used herein, the term "resistive force" shall mean the force necessary to deflect the tip 0.300 inches (0.762 cm).
3. As additional compressive forces are applied to the coil the force required to deflect the tip increases.

Pretensioned coils according to the present invention produce a significant increase in resistive force for the entire catheter assembly as compressive forces are increased. Resistive forces at 3 lb compressive force are at least 5% greater than the resistive forces measured at 0 lb compressive force (i.e. no load). Preferably, the resistive forces at 3 lb compressive force are at least 25% greater than the resistive forces measured at 0 lb compressive force.). Most preferably, the resistive forces at 3 lb compressive force are at least 50% greater than the resistive forces measured at 0 lb compressive force. This translates into a very stiff catheter assembly during the period when compressive forces are applied to push the catheter through the tough septum of a subcutaneous vascular access port. However, once compressive forces are no longer applied, the catheter assembly becomes more flexible. This provides the patient with a more comfortable infusion system. For example, a catheter according to the present invention fabricated from: a 0.030 inch inside diameter coil consisting of a 10 gauge stainless steel wire having a 2°–3° negative lead angle; a 0.028 inch outside diameter puncture needle; and a sheath formed from a Teflon tube having a wall thickness of 0.007 inch exhibits a resistive force at 3 lb compressive force of about 0.24 lb. as compared with a resistive force measured at 0 lb compressive force of about 0.18 lb.

Figure 9A:
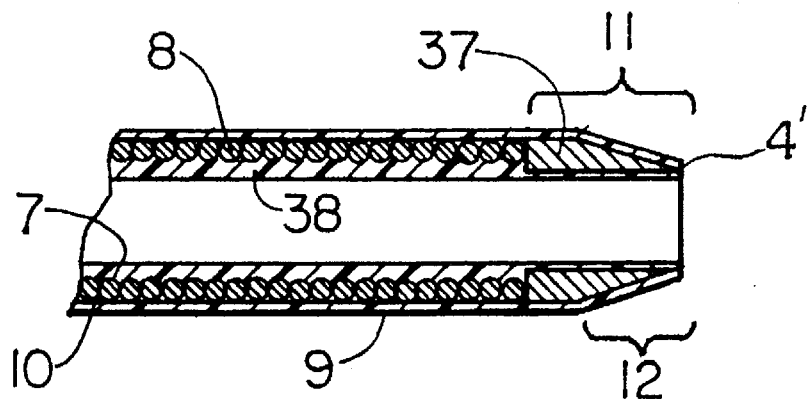
FIG. 9 is a longitudinal section of a helical coil catheter constructed in accordance with the principals of the present invention, which further includes a flexible plastic coating or liner inside the catheter.
Figure 9B:
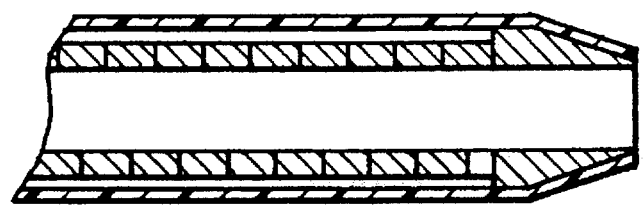

In an embodiment of the present invention the distal end of the coil 11 includes a bushing 37 (See FIG. 9a). Typically, the bushing is affixed to the end of the coil by a weld or other suitable connection means. This bushing aids in needle alignment during the puncturing operation. It is important that the bushing not be so long that it protrudes from the patient after the needle has been inserted into a subcutaneous vascular access port. Preferably, the bushing should be contained below the exterior surface of the subcutaneous access port septum. Another embodiment of the tip is shown in FIG. 9b. In FIG. 9b, the tip is solid formed with the inert tube sheath to form a firm penetrating tip that does not peel back.

The coil may be formed from stainless steel, Platinum, Tantalum, Tungsten, NITINOL™ nickel/titanium alloy, rigid fibers or other similar medically approved material and an outer sheathing 9 formed from a tube of smooth, inert flexible plastic material, such as TEFLON(R) fluorocarbon polymers, polyethylene, polypropylene, polyvinyl chloride or the equivalent thereof, that is heat-shrunk, mechanically-shrunk or a combination thereof over the coil in such a manner that the outer surface of the plastic tube remains smooth and its inner surface is forced into the spiral grooves on the outer surface of the coil 10; thus, effecting a firm attachment between the sheathing tube and the coil. For a detailed discussion of a suitable type of heat shrink processing see U.S. Pat. No. 4,044,765 to Kline, issued Aug. 30, 1977, incorporated herein by reference. Other methods of manufacture may also be used. For example, the surface of the coil could by dip-coated with suitable plastic, or, the outer sheath could be injection molded, such that the interior of the molded tube would have a spiral contour which accepts the outer contour of the coil in the same way a nut accepts a screw thread.

As shown in FIG. 9a, the interior of the catheter may also be coated with an inert flexible plastic coating 38. Methods of coating the inside of the cannula with a fluorinated hydrocarbon are found in U.S. Pat. No. 3,922,378 to Kline, issued Nov. 11, 1975 and U.S. Pat. No. 4,044,765 to Kline, issued Oct. 30, 1977, both incorporated herein by reference. Other methods of coating or lining the interior of the catheter known to those skilled in the art may also be utilized. Alternatively, a tube could be inserted down the lumen of the coil, either before or after the sheathing operation.

The distal end of the tubular sheathing extends distally beyond the distal end of the coil to define a distally extending straight tip 11 that is necked down as 12. As a result of the initial heat-shrinking or subsequent heat-drawing to lock the distal end of the coil against axial elongation, a smaller outer diameter for the tip is provided to enhance its ease of penetration through the skin and into the access port. In one embodiment, the distal end of the tip is heat-drawn or otherwise formed into a taper having a lip that is adapted to fit closely around an internal puncture needle. In the embodiment of FIG. 9, the bushing 37 extends from the distal end and forms the tip 12. Preferably, this tip is made of a transparent material. It is important that the tip 12 has sufficient strength so that it does not peel back upon insertion through the skin and into an access port septum.

For a discussion of various intravenous catheters which incorporated a coil guide mechanism see: U.S. Pat. Nos. 3,757,768; 3,841,308; 3,922,378; 4,044,765; 4,052,989; and 4,368,730, incorporated herein by reference.

The puncture needle 2 may be frictionally and slidably retained within the distal end of the catheter 4' by the necked-down tip 12, by the inner wall of the catheter 7 and/or by a membrane seal member 19 (not shown). The puncture needle 2 can be made of any medically acceptable material, including stainless steels, hard plastics, ceramics, carbon fibers, tantalum, tungsten or titanium. Preferably, the puncture needle is stainless steel. The puncture needle 2 is provided at its distal end 4 with a sharpened point to aid penetration. The point can be conical, a lancet cut. a trocar (3-sided point) cut, a diagonally cut cylinder (as shown) or any geometry suitable to achieve penetration through the skin and through a subcutaneous access port septum. The needle can be solid or cannulated (i.e. hollow, tubular, etc.). A cannulated puncture needle could be used to sample blood immediately upon insertion. Preferably, a cannulated puncture needle will utilize a Huber-style non-coring point. See, for example U.S. Pat. No. 4,954,130 to Edwards, incorporated herein by reference. Once it has been established that the tip of the assembly, 4 and 4', has entered the access port reservoir, the puncture needle 2 can be removed; thus, opening the cannula for fluid flow.

The proximal end of the catheter is provided with a hub member 6 which acts as a connecting means. In FIG. 3, the hub member 6 is a female luer fitting. Once the catheter assembly tip, 4 and 4' has been positioned in the access port reservoir and the puncture needle 2 removed, a small quantity of fluid is removed from the reservoir to purge the catheter cannula of air. Then infusion therapy is initiated.

An important feature of the present invention is the synergy which exists between the puncture needle 2 and the catheter 3. It is not essential that either alone be rigid enough to penetrate the tough silicone septum of an access port. These septa have Shore A hardnesses greater than 25, typically from 25 to 50. However, it is critical that the combination of puncture needle 2 and catheter 3 have sufficient stiffness to penetrate the tough, self-sealing, port septum 26 (not shown) into the reservoir. The needle locks the coils seriatim preventing the coil elements from moving radially to provide a minimum total stiffness corresponding to about the stiffness of a standard 22 gauge stainless steel needle. Once the penetration needle is removed, the coils become unlocked; thus, providing a catheter which is quite flexible. This flexibility adds a great deal of comfort to the patient.

Figure 6:
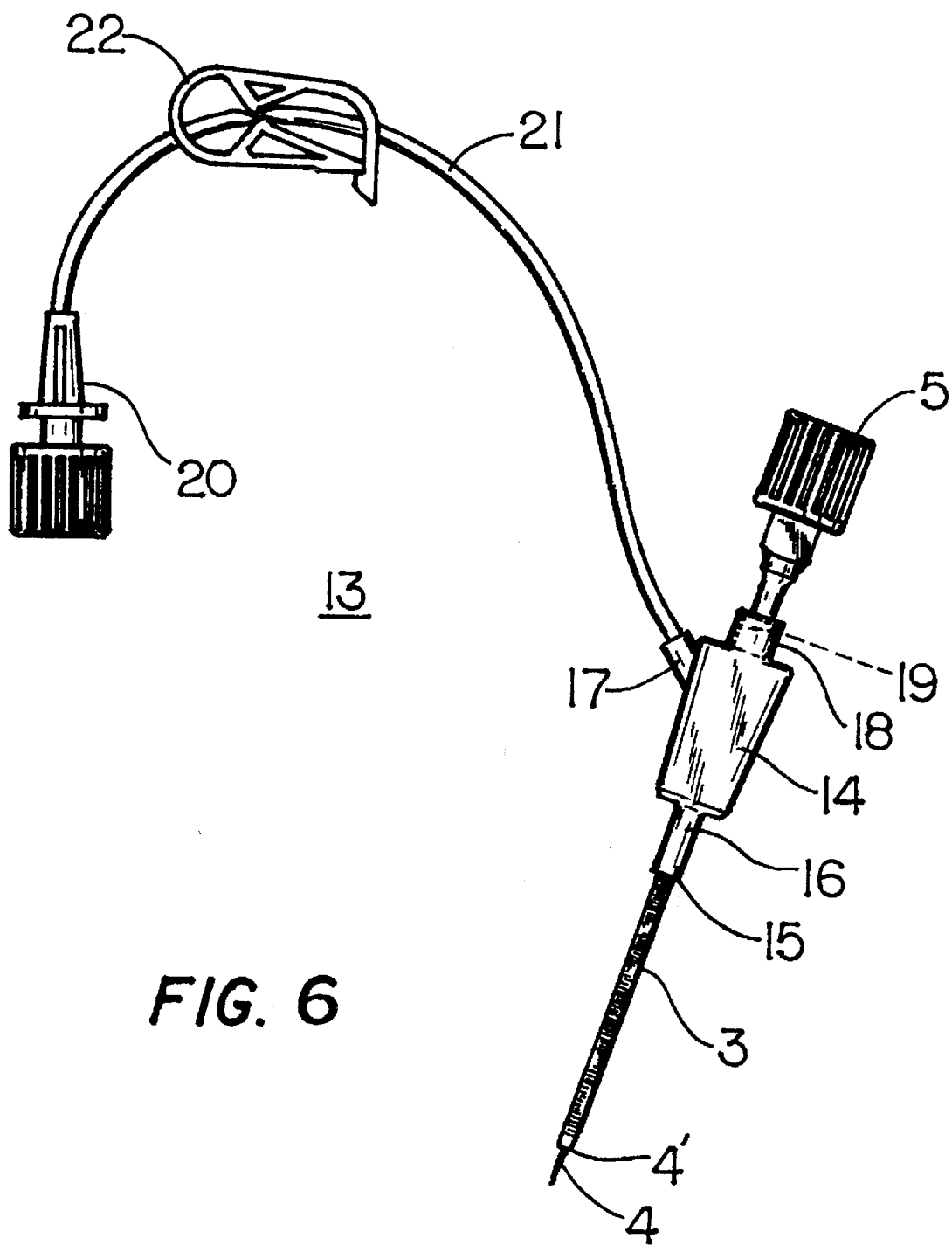
FIG. 6 is a perspective view of a preferred subcutaneous access port catheter assembly in accordance with the present invention.

FIG. 6 depicts a most preferred embodiment of the present invention. This figure shows a subcutaneous vascular access port catheter assembly 13 complete with still more ancillary features for ease of use. This device is particularly suited for use in subcutaneous vascular access port infusion therapy. The assembly comprises a puncture needle disposed within a flexible, single lumen catheter 3. The cannula assembly 13 utilizes a puncture needle 2 as described above. However, this most preferred embodiment replaces the hub connecting means 6 of the FIG. 3 embodiment with a hollow, junction housing member 14. As depicted, the housing member 14 forms a "y" junction. Other multiport housing junctions, such as "Y"-shaped, "+"-shaped or "T"-shaped junctions, may also be utilized, though they are not as desirable for most infusion therapies. The proximal end of the cannula 15 is affixed to the distal end of the housing 14 by any means known to those skilled in the art. Preferably, the cannula is affixed to the housing by means of adhesives, thermoplastic welds or a molded connection. The housing itself is preferably a plastic material. The most preferred housing materials include rigid clear plastics which allow for the observation of infused liquid. Clear plastics which are suitable for use in the present invention include LEXAN® carbonate-linked polymers. An alternate most preferred embodiment utilizes a contoured and flexible plastic housing which imparts greater comfort to the patient. Suitable flexible plastics include urethanes, thermoplastic elastomers, styrene/butadiene rubbers, etc. The housing has additional ports: one which is directed to the infusion liquid source 17; and one through which the proximal end (knob end) of the puncture needle exits 18. The needle exit port 18 has an integral membrane seal 19. This seal can be made from a variety of material, such as latex rubber or other self-sealing membrane-type materials. The preferred membrane seal is a silicone, plug-like member which is retained in the membrane seal port under compression. In practice, once the cannula needle tip is positioned within the reservoir of the access port (as described above), the puncture needle 2 is extracted from the cannula 3, providing access from the infusion source 17 through the housing 14 and into the vascular access port. Preferably, the needle 2 is totally extracted from the membrane seal 19. The seal holds against back pressure from the body and due to injection fluid pressure.

As can be seen from the depiction in FIG. 6, the infusion source port 17 on the housing member is connected to a hub 20 by way of a hollow flexible tube 21. The tube 21 is also equipped with a pinch clamp 22 to keep infusion liquid out of the housing prior to use and to prevent blood from flowing when no infusion liquid is flowing.

A most preferred embodiment of the FIG. 6 device has the following physical parameters:

| Cannula: | |
|---|---|
| Length: | 1.5 inches (38.1 mm) overall - allowing for a penetration depth into subcutaneous access port of about 0.5 inches (12.7 mm) |
| Diameter: | I.D. = 0.030 inches (0.76 mm) O.D. = 0.052 inches (1.32 mm) |
| Tip: | Smooth taper from O.D. for ease of penetration through port membrane. |
| Flexibility: | Can be taped down to the body without kinking. |

| | |
|---|---|
| Column Strength: | With penetration needle inserted, has the strength to pass through an access port septum without kinking or tip peelback. |
| Port Retention: | Catheter must maintain an integral connection within the access port septum, comparable to a standard needle for an indwelling period of up to 3 weeks. |
| Markings: | Graduated to show depth indications. |

"Y" Body Housing:

| | |
|---|---|
| Diameter: | 0.125 inches (3.175 mm) |
| Seal: | Must provide a water tight seal around puncture needle/flex catheter immediately upon insertion into the port septum. Must provide water tight seal against arterial blood pressures (about 150 mm Hg) and against syringe flush (about 100 psi) with puncture needle/flex catheter removed after storage for a period of 1 year. Must provide a water tight seal around 21 and 22 gauge needles after 30 punctures, with immediate seal integrity following their removal. |

The present invention also contemplates an entire transcutaneous infusion system which combines the above mentioned catheter assembly with a subcutaneous access port.

Figure 7:
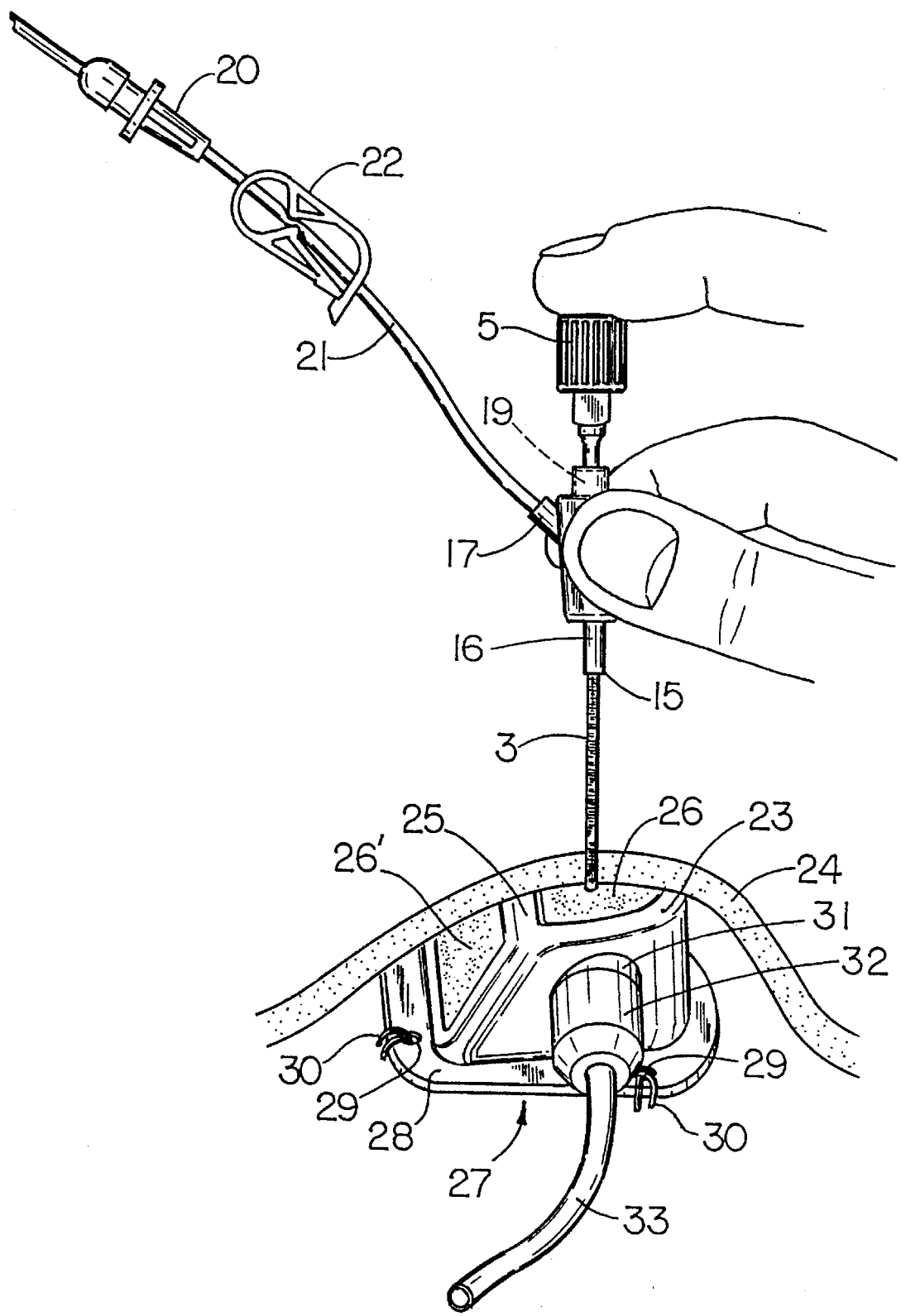
FIG. 7 depicts a manner in which the device of FIG. 6 may be inserted into a vascular access port.

FIG. 7 depicts the insertion of a device like the one presented in FIG. 5 into a subcutaneous vascular access port 23. The skin 24 has been partially removed for clarity. The subcutaneous access port 23 is surgically implanted beneath the skin 24 of a person or animal. The port is commonly formed to have a housing 25 to include a cavity which, when covered with a tough, self-sealing septum, encloses a reservoir. Housing 25 is made of a biocompatible and drug compatible material like titanium, stainless steel, polysulfone, or DELRIN® acetal resin. The septum 26 is permanently compressed and contained in the housing such that it forms a barrier between the internal reservoir and the exterior of the port 23. The septum 26 must be capable of staying under compression and not excessively creeping out of the port housing. The septum must also hold the catheter from dislodging. Typically, these septa will have a Shore A durometer of from about 25 to about 50 and a tear strength of about 200 Die B. Commercial septa of this type are made of silicone rubber or other elastomers. The port is oriented with the septum on an access side nearest the skin. Housing 25 then provides a solid surface 27 on a side opposite septum 26. Housing 25 can be mounted on another implanted medical device, e.g., an artificial organ or pump, or it can be mounted directly on a patient. In FIG. 7 the housing 25 is equipped with a flange 28 with a plurality of holes 29 through which sutures 30 may be passed to tie the port to muscle or other tissue. A sutured port is typically used as a subcutaneous vascular access port device wherein the housing further includes a passage 31 exiting the reservoir to a fitting 32 to which a tube 33 is fastened. The tube is typically directed to a vein (not shown).

Figure 8:
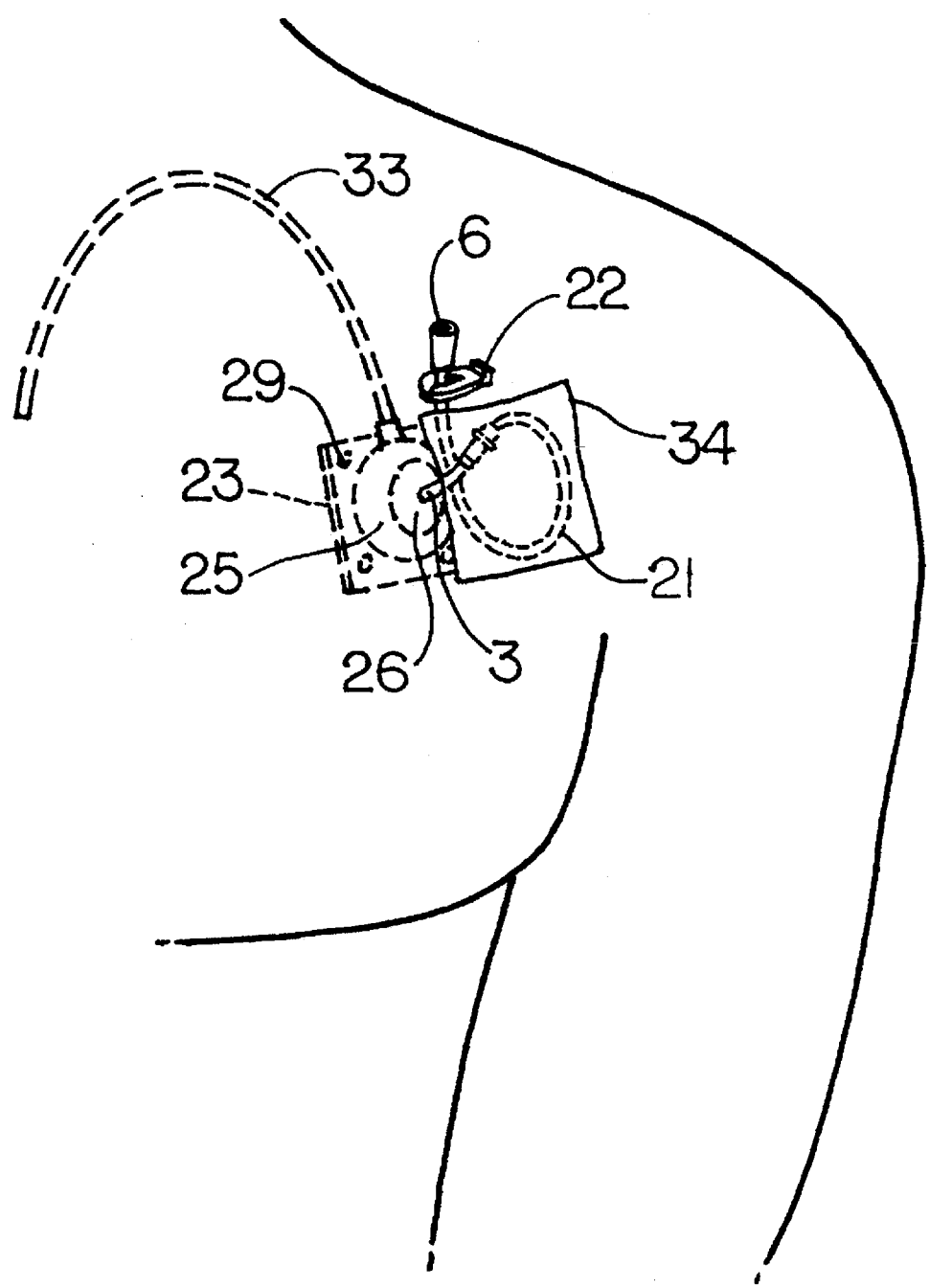
FIG. 8 depicts the device of FIG. 3 as it would look when inserted into a patient's subcutaneous access port.

FIG. 8 depicts a device like the one described in FIG. 3 which has been connected to a subcutaneous access port and has an infusion tubing attached. A small amount of adhesive bandage 34 is used as an added precaution against dislodging the catheter.

Although particular embodiments of the present invention have been shown and described, modifications may be made to the catheter assembly without departing from the teachings of the present invention. Accordingly, the present invention comprises all embodiments within the scope of the appended claims.

What is claimed is:

1. A subcutaneous access port catheter assembly comprising:

a flexible catheter, said catheter having distal and proximal ends and having an inner wall portion defined by a pretensioned, continuous helical coil and an outer sheathing formed from a tube of smooth, inert flexible plastic material, wherein said sheath is in intimate contact with the outer spiral of said coil; and an elongated puncture needle having a sharp point at the distal end and a knob member at the proximal end, said puncture needle being inserted coaxially down the length of said catheter such that the sharp point at the distal end of the elongated puncture needle extends beyond the distal end of said catheter, wherein the resistive force necessary to deflect the tip of a 1.4 inch length of catheter increases by at least about 5% as the compressive force on the catheter is increased from 0 lb. to 3 lb.

2. A subcutaneous access port catheter assembly according to claim 1 wherein the resistive force necessary to deflect the tip of a 1.4 inch length of catheter increases by at least about 25% as the compressive force on the catheter is increased from 0 lb. to 3 lb.

3. A subcutaneous access port catheter assembly according to claim 2 wherein the resistive force necessary to deflect the tip of a 1.4 inch length of catheter increases by at least about 50% as the compressive force on the catheter is increased from 0 lb. to 3 lb.

4. A subcutaneous access port catheter assembly according to claim 1 wherein said coil is produced by wire-wrapping at a negative lead angle.

5. A subcutaneous access port catheter assembly according to claim 4 wherein said coil is produced by wire-wrapping at a negative lead angle of from 0° to 4°.

6. A subcutaneous access port catheter assembly according to claim 5 wherein said coil is produced by wire-wrapping at a negative lead angle of from 2° to 3°.

7. A transcutaneous infusion system comprising:

a flexible catheter, said catheter having distal and proximal ends and having an inner wall portion defined by a pretensioned, continuous helical coil and an outer sheathing formed from a tube of smooth, inert flexible plastic material, wherein said sheath is in intimate contact with the outer spiral of said coil; and an elongated puncture needle having a sharp point at the distal end and a knob member at the proximal end, said puncture needle being inserted coaxially down the length of said catheter such that the sharp point at the distal end of the elongated puncture needle extends beyond the distal end of said catheter; and a subcutaneous access port comprised of a tough septum sealing one opening of an access port hollow housing, said access port housing further comprising an outlet port to permit fluid flow from the access port housing to an artery, vein or other distant body region by way of a surgically implanted flexible tube, wherein the resistive force necessary to deflect the tip of a 1.4 inch length of catheter increases by at least about 5% as the compressive force on the catheter is increased from 0 lb. to 3 lb.

8. A subcutaneous access port catheter assembly according to claim 7 wherein the resistive force necessary to deflect the tip of a 1.4 inch length of catheter increases by at least about 25% as the compressive force on the catheter is increased from 0 lb. to 3 lb.

9. A subcutaneous access port catheter assembly according to claim 8 wherein the resistive force necessary to deflect the tip of a 1.4 inch length of catheter increases by at least about 50% as the compressive force on the catheter is increased from 0 lb. to 3 lb.

10. A subcutaneous access port catheter assembly according to claim 7 wherein said coil is produced by wire-wrapping at a negative lead angle.

11. A subcutaneous access port catheter assembly according to claim 10 wherein said coil is produced by wire-wrapping at a negative lead angle of from 0° to 4°.

12. A subcutaneous access port catheter assembly according to claim 11 wherein said coil is produced by wire-wrapping at a negative lead angle of from 2° to 3°.

* * * * *